United States Patent [19]
Zacharie

[11] Patent Number: 5,457,180
[45] Date of Patent: Oct. 10, 1995

[54] METHODS FOR PRODUCING LINEAR THIOPEPTIDES USING AN AMINO ACID ORTHO AMINO THIOANILIDE COMPOUND

[75] Inventor: Boulos Zacharie, Rapides, Canada

[73] Assignee: Biochem Pharma Inc., Canada

[21] Appl. No.: 258,402

[22] Filed: Jun. 13, 1994

Related U.S. Application Data

[63] Continuation-in-part of Ser. No. 839,602, Feb. 21, 1992, Pat. No. 5,371,185, which is a continuation-in-part of Ser. No. 389,852, Aug. 4, 1989, Pat. No. 5,138,061.

[51] Int. Cl.$^6$ .............. C07K 7/02; C07K 7/04; C07K 7/06; C07K 7/08; C07K 7/10
[52] U.S. Cl. .............. 530/333; 564/74; 564/139
[58] Field of Search .............. 530/333; 564/514, 564/139

[56] References Cited

U.S. PATENT DOCUMENTS

| | | | |
|---|---|---|---|
| 2,676,969 | 4/1959 | Klingsberg et al. | 564/74 X |
| 3,334,083 | 8/1967 | Beyerman et al. | 530/333 |
| 3,499,085 | 3/1970 | Naraynan et al. | 548/305 |
| 3,830,794 | 8/1974 | Mukaiyama et al. | 530/333 |
| 3,901,909 | 8/1975 | Sasse et al. | 548/305 |
| 4,000,159 | 12/1976 | Scoggins et al. | 564/74 X |
| 4,145,352 | 3/1979 | Kubicek | 564/74 X |
| 4,935,510 | 6/1990 | Stahly | 540/490 |
| 5,013,759 | 5/1991 | Berman et al. | 514/622 |
| 5,041,653 | 8/1991 | Lee et al. | 564/74 |

FOREIGN PATENT DOCUMENTS

| | | | |
|---|---|---|---|
| 222283 | 5/1987 | European Pat. Off. | 548/305 |
| 56-29552 | 3/1981 | Japan | 564/74 |
| 70-02555 | 8/1970 | Netherlands | 564/74 |

OTHER PUBLICATIONS

Brown et al., Tetrahedron Letters, vol. 28 (19), pp. 2171 to 2174 (1987).
Clausen et al. I. Tetrahedron, vol. 37 (21), pp. 3635 to 3639 (1981).
Clausen et al. II, Chem. Soc. Perkin Trans I, vol of 1984, pp. 785 to 798.
Jensen et al., Tetrahedron, vol. 42 (23), pp. 6555 to 6564 (1986).
Wajoie et al., Tetrahedron Letters, vol. 24(36), pp. 3815 to 3818 (1983).
O. K. Archer et al., "Reduced Antibody Response In Thymectomized Rabbits", Nature, 195, pp. 191–193 (1962).
P. A. Bartlett et al., "A Thioamide Substrate Of Carboxypeptidase A", Biochemistry, 21, pp. 1608–1611 (1982).
B. Belleau and G. Malek, I "A New Convenient Reagent for Peptide Synthesis", J. Am. Chem. Soc., 90, pp. 1651–1652 (1968).
B. Belleau et al., II "Some Remarkable Effects of Thiopeptide and Derived Linkages on Lysozyme Release from Neutrophils by Esters of the Chemotactic Peptide N–Formyl–Methionyl–Laucyl Phenylalanine (f–Met–Leu–Phe–OR)", Int. J. Immunopharmac., 11, pp. 467–471 (1989).

D. W. Brown et al., "Mono–and Dithionopeptide Synthesis", Tetrahedron Letters, 28(19), pp. 2171–2174 (1987).
P. Campbell and N. T. Nashed, "Carboxypeptidase A Catalyzed Hydrolysis Of Thiopeptide And Thionester Analogues Of Specific Substrates. An Effect On $k_{cat}$ For Peptide, But Not Ester, Substrates", J. Am. Chem. Soc., 104, pp. 5221–5226 (1982).
K. Clausen et al., I "Evidence Of A Peptide Backbone Contribution Toward Selective Receptor Recognition For Leucine Enkephalin Thioamide Analogs", Biochem. Biophys. Res. Comm., 120, pp. 305–310 (1984).
K. Clausen et al., "Studies On Amino Acids And Paptides. Part 6. Methods For Introducing Thioamide Bonds Into The Peptide Backbone: Synthesis Of The Four Monothio Analogues Of Leucine Enkephalin", J. Chem. Soc. Perkin Trans. I, pp. 785–798 (1984).
K. Clausen et al., III "Role of the Peptide Backbone in Biological Activity: Synthesis of Enkephalins with Psi ($CH_2$) and Psi (CSNH) Amide Bond Replacements", Pept.: Struct. Funct. Proc. Am. Pept. Symp. (8th), pp. 307–310 (1983).
K. Clausen et al., IV "Synthesis of Leucine Enkephaline and Aspartame Analogs Containing Thioamide Linkages at Specific Positions", Pept. Proc. Eur. Pept. Symp. (17th), pp. 207–210 (1982).
A. R. Katrinsky et al., "Azlactones as Polymer Components and Intermediates", J. Polym. Sci. Polym. Chem. Ed., 27(5), pp. 1781–1790 (1989).
G. Lajoie et al., "Synthesis and Biological Activity Of (List continued on next page.)

Primary Examiner—Floyd D. Higel
Attorney, Agent, or Firm—Fish & Neave; James F. Haley, Jr.; Andrew S. Marks

[57] ABSTRACT

The present invention provides methods for producing linear thiopeptides using an amino acid ortho amino thioanilide compound of formula (III)

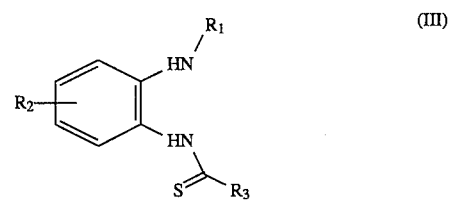

(III)

wherein
$R_1$ is selected from the group consisting of hydrogen or $C_1$–$C_4$ branched or unbranched alkyl;
$R_2$ is selected from the group consisting of hydrogen, halo, amino, hydroxy, $C_1$–$C_4$ branched or unbranched alkoxy, guanido, amido, acyl, carboxy, cyano, mercapto, nitro, azido, and $C_1$–$C_4$ branched or unbranched alkyl optionally substituted by halo, amino, hydroxy, $C_1$–$C_4$ branched or unbranched alkoxy, guanido, amido, acyl, carboxy, cyano, mercapto, nitro, azido;
$R_3$ is a decarboxylated amino acid residue or a decarboxylated amino acid chain comprising at least two amino acid residue.

24 Claims, No Drawings

OTHER PUBLICATIONS

Monothionated Analogs Of Leucine–Enkephalin"*Int. J. Pept. Prot. Res.,* 24, pp. 316–327 (1984).

C. Y. Lau and G. Goldstein, "Functional Effects Of Thymopoietin$_{32-36}$ (TP5) On Cytotoxic Lymphocyte Precursor Units (CLP–U). I. Enhancement Of Splenic CIP–U In Vitro And In Vivo After Subooptimal Antigenic Stimulation", *J. Immunol.,* 124, pp. 1861–1865 (1980).

L. Maziak et al., "Productive Conformation In The Board State And Hydrolytic Behavior Of Thiopeptide Analogues Of Angiotensin–Converting Enzyme Substrates", *J. Am. Chem. Soc.,* 108, pp. 182–183 (1986).

R. B. Merrifield, "Solid Phase Peptide Synthesis. I. The Synthesis Of A Tetrapeptide", *J. Am. Chem. Soc.,* 85, pp. 2149–2154 (1963).

W. L. Mock et al., "Hydrolysis of a Thiopeptide by Cadmium Carboxypeptidease A.", *Biochem. Biophys. Res. Commun.,* 102(1), pp. 389–396 (1981).

D. Osoba and J. F. A. P. Miller, "Evidence For A Humoral Thymus Factor Responsible For The Maturation Of Immunlogical Faculty", *Nature,* 199, pp. 653–654 (1963).

G. E. Ranges et al., "T Cell Development In Norman And Thymopentin–Treated Nude Mice", *J. Exp. Med.,* 156, pp. 1057–1064 (1982).

W. Ried and E. Schmidt, "N–Acylierte α–Aminoimisäureester, Iminodipeptide Und Endothiodipeptide", *Liebigs Ann. Chem.,* 695, pp. 217–225 (1966).

W. Ried and W. von der Emden, "Aminosaure–Thionester Und Endothiopeptide, II", *Liebigs Ann. Chem.,* 642, pp. 128–133 (1961).

S. Salvadori et al., "Opioid Peptides. Structure–Activity Relationships of Dermorphin Endothiotetrapeptides", *Farmaco Ed. Sci.,* 39(4), pp. 316–321 (1984).

D. B. Sherman et al., "Compatibility of Thioamides With Reverse Turn Features: Synthesis and Conformational Analysis of Two Model Cyclic Pseudo–Peptides Containing Thioamides As Backbone Modifications", *J. Am. Chem. Soc.,* 112(1), pp. 433–441 (1990).

METHODS FOR PRODUCING LINEAR THIOPEPTIDES USING AN AMINO ACID ORTHO AMINO THIOANILIDE COMPOUND

This application is a continuation-in-part of U.S. patent application Ser. No. 07/839,609, filed Feb. 21, 1992, now U.S. Pat. No. 5,371,185 which is a continuation-in-part of U.S. patent application Ser. No. 07,389.852, filed Aug. 04, 1989, U.S. Pat. No. 5,138,061.

TECHNICAL FIELD OF THE INVENTION

This invention relates to method for producing linear thiopeptides using an amino acid ortho amino thioanilide.

BACKGROUND OF THE INVENTION

The biological utility of linear synthetic peptides is dramatically circumscribed by their short half-lives in vivo and their lack of effectiveness when administered orally. These therapeutic disadvantages are primarily due to the extreme lability of biologically active peptides in the presence of the peptidases and proteases normally found in the digestive tract.

It is, therefore, desirable to stabilize the biologically active peptides against destructive enzymes, such as proteolytic enzymes, in order to improve the pharmacokinetic properties of these peptides. Enhanced stability to enzymatic degradation would also make such peptides more useful as therapeutic agents.

One way to stabilize peptides is to stabilize their backbone amide linkages. Recent advances in chemical replacement and modification of peptide linkages indicate that such linkage stabilization is feasible. In one method, replacement of peptide linkages at positions amenable to peptidase and protease cleavage with thioamide bonds produces analogues that are more stable to enzymatic degradation.

These analogues also display enhanced pharmacological activity. See, for example, G. Lajoie et al., "Synthesis and Biological Activity of Monothionated Analogs of Leucine-enkephalin", *Int. J. Pept. Protein Res.*, 24, p. 316, (1984). Thiopeptide derivatives have also demonstrated increased activity in vivo as biological response modifiers, neuroeffectors, and immunomodulators, as compared with their oxygenated analogs. K. Clausen et al., "Evidence of a Peptide Backbone Contribution Toward Selective Receptor Recognition for Leucine Enkephalin Thioamide Analogs", *Biochem. Biophys. Res. Commun.*, 120, p. 305, (1984).

One method for forming a thioamide bond involves replacing the carbonyl oxygen of the native peptide bond with a sulphur. See, for example, K. Clausen et al., "Studies on Amino Acids and Peptides. Part 6. Methods for Introducing Thioamide Bonds into the Peptide Backbone: Synthesis of the Four Monothio Analogues of Leucine Enkephalin", *J. Chem. Soc. Perkin Trans.*, pp. 785–98 (1984) which describes a method of thioacylation using dithioesters to replace the carbonyl oxygen atom with a sulfur atom.

However, the known thioacylation methods suffer from several disadvantages. First, the syntheses of the prior art thioacylating reagents are cumbersome and difficult. Furthermore, these syntheses produce low overall yields of the desired thiopeptide and often produce significant amounts of undesired and difficult to remove by-products. The prior art syntheses are also disadvantageous in that they can only be carried out on a small scale due to difficult purification schemes and extremely toxic reagents.

Finally, the optical integrity of thiopeptides produced by these prior art methods is often not maintained. This further reduces the potential use of the thiopeptides as pharmacological agents.

For the reasons recited above, there is a need for a thioacylating process which can provide the formation of linear thiopeptides. In addition, there is a need for a thioacylating process which can be run on a large scale while producing thiopeptides in high overall purity and yield. There is also a need for a thioacylating process which will retain the optical integrity of the product thiopeptides. There is also a need for thiopeptides which demonstrate superior biologically useful characteristics, such as increased resistance to enzymatic degradation and improved pharmacological activity.

SUMMARY OF THE INVENTION

It is an object of this invention to provide method for producing linear thiopeptides.

The method of this invention for producing a linear thiopeptide comprises step 3):

contacting a peptide or an amino acid residue with a mixture comprising an amino reactive compound in an inert solvent (a) and an amino acid ortho amino thioanilide of formula (III):

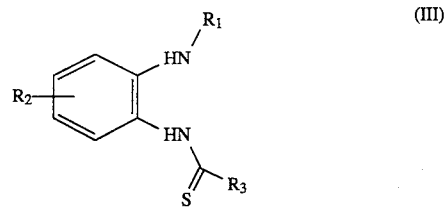

wherein
- $R_1$ is selected from the group consisting of hydrogen, $C_1$–$C_4$ branched or unbranched alkyl, and an appropriate amino protecting group such as t-butyloxycarbonyl (Boc), benzyl, or benzyloxycarbonyl (CbZ);
- $R_2$ is selected from the group consisting of hydrogen, halo, amino, hydroxy, $C_1$–$C_4$ branched or unbranched alkoxy, guanido, amido, acyl, carboxy, cyano, mercapto, nitro, azido, and $C_1$–$C_4$ branched or unbranched alkyl optionally substituted by halo, amino, hydroxy, $C_1$–$C_4$ branched or unbranched alkoxy, guanido, amido, acyl, carboxy, cyano, mercapto, nitro, azido; and
- $R_3$ is a decarboxylated amino acid residue or a decarboxylated amino acid chain comprising at least two amino acid residue.

The synthesis of the amino acid ortho amino thioanilide compound of formula (III) comprises step 2): contacting an amino acid ortho amino anilide intermediate of formula (II):

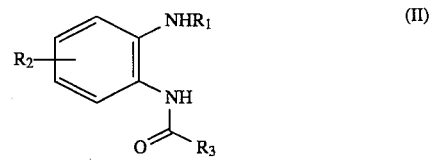

wherein $R_1$, $R_2$ and $R_3$ are as defined above; with a thionation reagent in an inert organic solvent (b).

The amino acid ortho amino anilide intermediate of formula (II) is produced by step 1): contacting $R_3COOH$ with an orthophenylene diamine of formula (I):

SCHEME 1

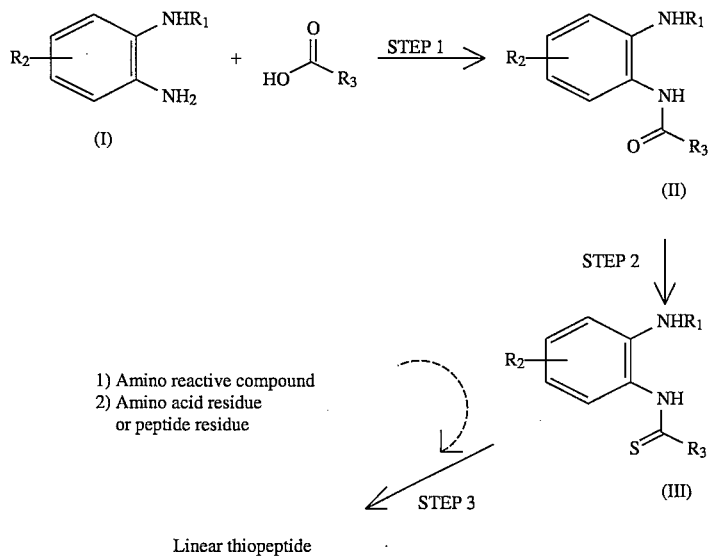

1) Amino reactive compound
2) Amino acid residue
or peptide residue

Linear thiopeptide

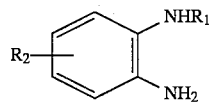

wherein $R_1$, $R_2$, and $R_3$ are as defined above; in presence of a peptide coupling agent in inert organic solvent (c).

DETAILED DESCRIPTION OF THE INVENTION

In accordance with this invention, the following definitions apply:

amino acid or amino acid residue—a chemical moiety having an N-terminus and a C-terminus (being either a C=O or C=S terminus) separated by a single carbon atom. As used herein, 'amino acid' refers either to the free, unbound form, the form bound by either a peptide or a thiopeptide bond at a single terminus (either the N-terminus or the C-terminus) or the form bound at both the N- and the C-termini via peptide or thiopeptide bonds. This term encompasses all of the naturally occurring amino acids, those amino acids in their D-configurations, and nonnative, synthetic and modified amino acids such as homocysteine, homoserine, diaminobutyric acid, ornithine, norleucine and 2-amino-5-hydroxy pentanoic acid. The term 'amino acid' also includes those carrying side chains which are protected with any protecting group, as well as the unprotected or deprotected, free form.

peptide—two or more amino acid residues covalently bound via a peptide bond. A peptide is also called an amino acid chain.

thiopeptide—two or more amino acid residues covalently bound via peptide bonds, at least one of which is a thiopeptide bond.

halo—a chemical moiety selected from the group consisting of fluoro, chloro, bromo and iodo.

Scheme 1 depicts the preferred method for producing a thiopeptide using an amino acid ortho amino thioanilide of formula (III).

wherein $R_1$ is selected from the group consisting of hydrogen, $C_1-C_4$ branched or unbranched alkyl, and an appropriate amino protecting group such as t-butyloxycarbonyl (Boc), benzyl, and benzyloxycarbonyl (CbZ);

$R_2$ is selected from the group consisting of hydrogen, halo, amino, hydroxy, $C_1-C_4$ branched or unbranched alkoxy, aryl, amido, acyl, carboxy, cyano, mercapto, nitro, azido, and $C_1-C_4$ branched or unbranched alkyl optionally substituted by halo, amino, hydroxy, $C_1-C_4$ branched or unbranched alkoxy, guanido, amido, acyl, carboxy, cyano, mercapto, nitro, or azido; and $R_3$ is the residue of $R_3COOH$, an amino acid, or an amino acid chain or peptide consisting of at least two amino acid residues. The various steps as illustrated in scheme 1 may be briefly described as follows.

As the above scheme demonstrates, an ortho-phenylene diamine (I) and $R_3COOH$ may be reacted in the presence of a peptide coupling agent to form an amino acid ortho amino anilide (II). Surprisingly, however, in this reaction, selective amide formation occurs at only one of the two amino substituents on the benzene ring. Contacting II with a thionation reagent forms an amino acid ortho amino thioanilide (III). Subsequent treatment of III with an amino reactive compound followed by a coupling with an amino acid residue or an amino acid chain to yield to a linear thiopeptide.

STEP 1

Coupling of an ortho-phenylene diamine (I) with $R_3COOH$, as described above, may be accomplished by employing established techniques in the field of peptide chemistry. A broad range of suitable reactions are described in E. Gross & J. Meinhofer, *The Peptides: Analysis, Syn-* thesis, Biology; Modern Techniques of Peptide and Amino Acid Analysis, (John Wiley & Sons, 1981) and M. Bodanszky, Principles Of Peptide Synthesis, (Springer-Verlag, 1984). The peptide coupling agents which may, for example, be used include 1-3(3-dimethylaminopropyl)-3-ethylcarbodiimide hydrochloride (EDC), N,N'-dicyclohexylcarbodiimide (DCC), N,N'-carbonyl diimidazole (CDI), 1-hydroxy benzotriazole (HOBt) and ethyl chloroformate. The preferred coupling reagent is DCC. DCC may be used with or without catalytic additives such as 4-dimethylaminopyridine (DMAP), copper (II) chloride or HOBt. Such catalysts may increase the rate of reaction while suppressing the racemization of the desired compound. The use of DCC together with DMAP is preferred. The use of EDC with HOBt is most preferred. Racemization can also be prevented by using appropriated reaction conditions. For example, by carrying the reaction at low temperature.

The preferred, DCC/DMAP catalyzed reaction is typically performed in a solvent that is inert with respect to the reactants. The solvent is normally an organic solvent which is polar and aprotic. Preferred solvents include dichloromethane, chloroform, diethyl ether, tetrahydrofuran (THF) and N,N'-dimethylformamide (DMF). Particularly preferred solvents are dichloromethane and DMF. The coupling reaction is run under atmospheric pressure at a temperature of −78° C. to reflux for a period of about 1–48 hours. Preferably, the reaction is carried out at −10° C. to 25° C. with stirring, shaking or agitation over a period of 4–6 hours.

The most preferred EDCHOBt catalysed reaction is typically performed in a solvent that is inert with respect to the reactants. The solvent is normally an organic solvent which is polar and aprotic. Preferred solvents include dichloromethane, chloroform, diethyl ether, tetrahydrofuran (THF) and N,N'-dimethylformamide (DMF). Particularly preferred solvents are dichloromethane DMF and THF. The coupling reaction is run under atmospheric pressure at a temperature of −78° C. to reflux for a period of about 1–48 hours. Preferably, the reaction is carried out at −10° C. to 25° C. with stirring, shaking or agitation over a period of 4–6 hours.

STEP 2

Compounds of formula III are typically prepared under anhydrous conditions, by reacting intermediates of formula II with a mixture of phosphorous pentasulfide and anhydrous sodium carbonate in an inert solvent. The solvent is preferably anhydrous THF but other suitable solvents include dichloromethane, diethyl ether and DMF. The reaction temperature is preferably about 0° C., but may be varied from −78° C. to gentle reflux.

Compounds of formula (III) can also be prepared using Lawesson's reagent. Methods for using Lawesson's reagent are well known for persons skilled in the art. It would be preferable to protect one of the reactive amino function of the intermediate of formula (II) in order to obtain a reasonable yield of the desired compound of formula (III). A variety of protecting groups known in the field of peptide synthesis for reactive functional groups may be found in T. Greene, Protective Groups In Organic Synthesis, (John Wiley & Sons, 1981). The appropriate protecting group to use in a particular synthetic scheme will depend on many factors, including the presence of other reactive functional groups and the reaction conditions desired for removal as well known by persons skilled in the art of peptide chemistry.

STEP 3

Linear thiopeptide may be synthesized directly by contacting an amino acid ortho amino thioanilide compound of formula (III) with an amino reactive compound such as thiocarbonyldiimidazole in a inert solvent such as tetrahydrofuran followed by a coupling with a growing peptide residue or an amino acid residue at a temperature of −78° C. to gentle reflux, preferably room temperature. The resulting product is a linear thiopeptide.

As will be appreciated by one of skill in the art, residue $R_3$ of peptide $R_3COOH$ must be protected during the above-described reactions. The protecting groups are then removed at appropriate points in the reaction scheme, i.e., to allow cyclization or coupling of the peptide. As known in the art the protecting groups should be capable of introduction to $R_3$ efficaciously and their removal should be performed under conditions which do not adversely affect other portions of the molecule. In this manner, certain reactions and modifications may be performed with assurance that the protected functionality will not interfere with the desired reaction. Further, by choosing a protecting group that is sensitive and labile to certain reactive conditions, a reaction scheme may be outlined to easily and efficiently remove the protecting group once the synthesis is complete.

As it was mentioned previously, a variety of protecting groups known in the field of peptide synthesis for reactive functional groups may be found in T. Greene, Protective Groups In Organic Synthesis, (John Wiley & Sons, 1981). The appropriate protecting group to use in a particular synthetic scheme will depend on many factors, including the presence of other reactive functional groups and the reaction conditions desired for removal as well known by persons skilled in the art of peptide chemistry.

In the synthetic method described above, the desired products may be isolated from the reaction mixture by crystallization. Alternatively, other techniques may be used alone, or in addition to crystallization. Such additional techniques include chromatographic separations (for example, normal phase, reverse-phase, ion-exchange, affinity and gel permeation), as well as electrophoresis, extraction and other known means.

In a preferred embodiment, the method of this invention for producing linear thiopeptides comprises step 3):

contacting a peptide or an amino acid residue with a mixture comprising an amino reactive compound in an inert organic solvent (a) and amino acid ortho amino thioanilide of formula (III):

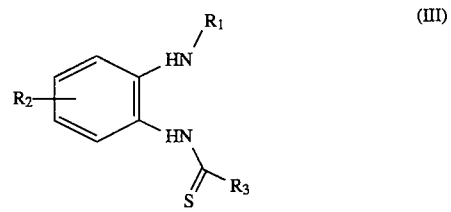

wherein $R_1$, $R_2$ and $R_3$ are defined above.

$R_1$ is preferably hydrogen.

$R_2$ is preferably hydrogen or an electron withdrawing substituent. The preferred electron withdrawing substituents include amido, halo, aryl, acyl, carboxy, cyano, nitro and azido. Use of an electron withdrawing substituent adjusts the degree of activation afforded to the thiocarbonyl carbon. By altering this activation level, difficult cyclization reactions may be driven towards completion, without sacrificing reaction-site specificity or forming undesired polymerization by-products.

$R_3$ preferably comprises between 1 and 15 amino acid residues and is the residue of $R_3COOH$. Preferably $R_3COOH$ contains naturally occurring amino acids. For the sake of clarity, as referred to herein, the position of each amino acid residue $R_3COOH$ may be referred to by a number, in ascending order, position 1 being the residue attached directly to the COOH moiety.

The synthesis of the amino acid ortho amino thioanilide compound of formula (III) is carried by step 2):

contacting an amino acid ortho amino anilide intermediate of formula (II):

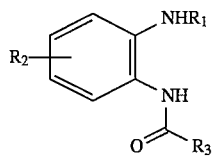
(II)

wherein $R_1$, $R_2$ and $R_3$ are as defined above;
with a thionation reagent in an inert organic solvent (b).

The amino acid ortho amino anilide intermediate of formula (II) is produced by step 1):

contacting $R_3COOH$ with an orthophenylene diamine of formula (I):

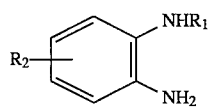
(I)

wherein $R_1$, $R_2$, and $R_3$ are as defined above;
in presence of a peptide coupling agent in inert organic solvent (c).

Linear thiopeptides may be synthesized using the methods of this invention by directly mixing the growing peptide residue or the amino acid residue with a compound of formula (III) and an amino reactive compound in an inert organic solvent. The amino reactive compound is preferably thiocarbonyldiimidazole, carbonyldiimidazole, carbonylditriazole, thiocarbonylditriazole or phosgene. The inert organic solvent (a) is preferably dichloromethane, diethyl ether, dimethylformamide, chloroform or tetrahydrofuran. The coupling reaction of step (3) is run under atmospheric pressure at a temperature of −78° C. to reflux for a period of about 1–48 hours. Preferably, the reaction is carried out at −10° C. to 25° C. with stirring, shaking or agitation over a period of 4–6 hours.

In a preferred embodiment, the thionation reagent is phosphorus pentasulfide and sodium carbonate or Lawesson's reagent and the inert organic solvent (b) is dichloromethane, diethyl ether, dimethylformamide, chloroform or tetrahydrofuran. The coupling reaction of step (2) is run under atmospheric pressure at a temperature of −78° C. to reflux for a period of about 1–48 hours. Preferably, the reaction is carried out at −10° C. to 25° C. with stirring, shaking or agitation over a period of 4–6 hours.

The inert organic solvent (c) is preferably dichloromethane, diethyl ether, dimethylformamide, chloroform or tetrahydrofuran. The coupling reaction of step (1) is run under atmospheric pressure at a temperature of −78° C. to reflux for a period of about 1–48 hours. Preferably, the reaction is carried out at −10° C. to 25° C. with stirring, shaking or agitation over a period of 4–6 hours.

Until the thioamide linkage is required to be introduced into a growing polypeptide chain or to an amino acid residue, the peptide may be synthesized under any peptide coupling conditions. Alternatively, the amino acid ortho amino thioanilide compound of formula (III) may be introduced first and the thiopeptide so formed may then be enlarged employing generally recognized peptide coupling conditions. However, it is most advantageous to first synthesize $R_3COOH$ so as to include all amino acid residues derived in the ultimate thiopeptide following the thioamide linkage. In this embodiment, addition of the amino acid ortho amino thioanilide compound of formula (III) to a solution of the growing peptide completes the desired thiopeptide. Because formation of the thioamide linkage requires only a single coupling step, optical purity of the final peptide is most easily monitored and maintained in this manner. In addition, overall yields and reaction-site specificity are improved. Also, product characterization is facilitated because the final thiopeptide may be formed from two well characterized fragments.

Once the product thiopeptide is formed, it may be freed of its protecting groups according to well-known protocols such as treatment with liquid hydrogen fluoride (HF). Where, however, selective removal of the protective groups, such as from the amino terminus only is desired, suitable reaction conditions must be employed. Those conditions are also well known in the art.

An alternative synthetic approach for introducing thioamide linkages to peptides using the methods of this invention is Merrifield solid phase synthesis and its known variants. Thus, a Merrifield resin is prepared by well-known solid phase peptide synthetic methods. A covalently attached α-amino acid residue, attached at its C terminus or, similarly, a peptide with a free terminal amino functionality is carried by the resin. Treatment of the resin with a amino acid ortho amino thioanilide compound of formula (III) according to this invention under standard conditions will afford the desired product in a single step, if, as is preferred, the $R_3$ residue includes all of the desired amino acids downstream of the thioamide bond. Alternatively, elongation of the thiopeptide chain may continue after the thioamide linkage is formed. Thioamide linkages using these amino acids ortho amino thioanilide compounds of formula (III) can also be introduced into peptides in automated peptide synthesizers using established synthetic techniques.

The completed thiopeptide may be liberated from the resin by using well-established methods. After freeing the thiopeptide from the resin, it may be deprotected as above.

In order that this invention be more fully understood, the following examples are set forth. These examples are for the purpose of illustration only, and are not to be construed as limiting the scope of the invention in any way.

In each example, reaction concentrations are generally held at 0.1M of the reactants, but a higher or lower concentration may be used in cases where the specific reaction is favorably influenced. In practice, the amounts of reagents will change depending upon variations in reaction conditions and the nature of the reactants themselves.

EXAMPLES

EXAMPLE 1

Synthesis of N-(Boc-Alanyl)-2-Benzimidazolone a) Boc-Alanyl-2-Aminoanilide

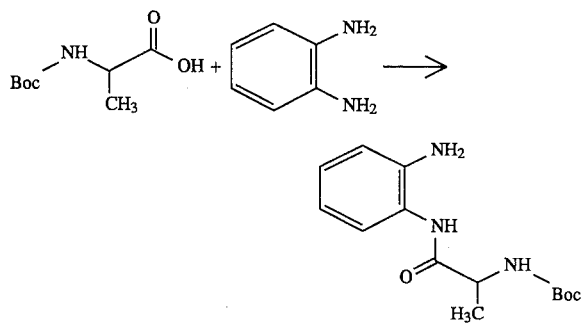

1-(3-dimethylaminopropyl)-3-ethylcarbodiimide hydrochloride (EDC) (2.10 G; 11 MmOL) was added to a mixture of Boc-L-Ala-OH (2.08 g; 11 mmol), 1,2-phenylenediamine (1 g; 9.2 mmol) and triethylamine (1.5 ml; 11 mmol) in $CH_2Cl_2$ (50 ml) at 0° C. After stirring at this temperature for two hours and then at room temperature overnight, 5% HCl (25 ml) was added and the mixture was washed with brine, 5% sodium bicarbonate, and brine, and dried over $Na_2SO_4$. Evaporation of the solvent and crystallization of the residue from $CH_2Cl_2$/hexanes afforded pure Boc-Alanyl-2-Aminoanilide (2.4 g; 94%) as a colorless solid m.p. 122°–24° C.; $R_f$=0.64 (EtOAc/hexanes 1), $^1$H NMR ($CDCl_3$) δ1.46 (d, 3H, J=6 Hz), 1.47 (s, 9H, 3×$CH_3$ Boc), 3.00 (bs, 2H, $NH_2$), 4.29 (m, 1H, $H^α$), 5.04 (d, 1H, NH, J=4.55 Hz), 6.78 (m, 2H, aromatic), 7.05 (m, 1H, aromatic), 7.26 (m, 1H, aromatic), 7.96 (bs, 1H, NH).

b) N-(Boc-Alanyl)-2-Benzimidazolone

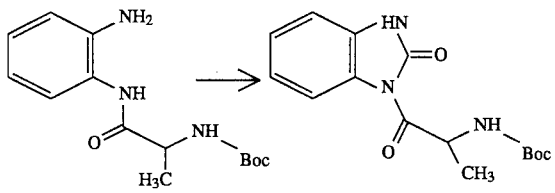

A solution of 1,2,4-triazole (0.25 g; 3.62 mmol) in dry THF (40 ml) was mixed with triphosgene (0.18 g; 0.61 mmol) and triethylamine (0.52 ml; 3.65 mmol ) under a flow of argon. The mixture was refluxed for 2 hours then cooled to room temperature. To this solution was added Boc-Alanyl-2-Aminoanilide (from a) (0.50 g; 1.81 mmol) and the reaction was stirred overnight at 25 ° C. Insolubles were removed by filtration and the solvent was evaporated under reduced pressure. The residue was chromatographed on silica gel using EtOAc: hexanes (1:1 ) as eluant. This gave pure Boc-Alanyl-2-Aminoanilide (0.34 g; 62%) as a white solid. $R_f$=0.52 (EtOAc/hexanes 2:3), $^1$H NMR ($CDCl_3$) δ1.47 (s, 9H, 3×$CH_3$ Boc), 1.51 (d, 3H, $CH_3$, J=7.02 Hz), 5.34 (d, 1H, NH, J=7.02 Hz), 5.70 (m, 1H, $H^α$), 6.9–7.1 (m, 3H, aromatic), 7.99 (d, 1H, aromatic), 9.31 (bs, 1H, NH). This compound was characterized as the hydrochloride salt. Thus, Boc-Alanyl-2Aminoanilide (0.12 g; 0.39 mmol ) was dissolved in dry ether (30 ml) at room temperature under argon. HCl gas was bubbled through this solution for ten minutes and the reaction mixture was stirred for one hour at this temperature. The solution was then evaporated to half of its volume and kept at 4° C. for four hours. The precipitate was collected and washed with cold dry ether (10 ml). This gave the hydrochloride salt of Alanyl-2-Aminoanilide (0.081 g; 86%) as a white solid: mp 52° C. (d), $R_f$=0.28 (20% MeOH/EtOAc), $^1$H NMR (DMSO) δ1.52 (d, 3H, $CH_3$, J=6.26 Hz), 5.09 (m, 1H, $H^α$) 7.09–7.27 (m, 3H, aromatic), 8.01 (d, 1H, aromatic, J=7.69 Hz), 8.48 (b, 3H, $NH_3$), 11.76 (s, 1H, NH), MS (FAB, thyioglycerol, m/e), 206 (M+1), HRMS m/e Calcd for $C_{10}H_{12}N_3O_2$ 206.0931, Found 206.0949.

EXAMPLE 2

SYNTHESIS OF N-(Boc-ThioAlanyl)-2-Benzimidazolone a) Boc-Alanyl-2-Aminothioanilide

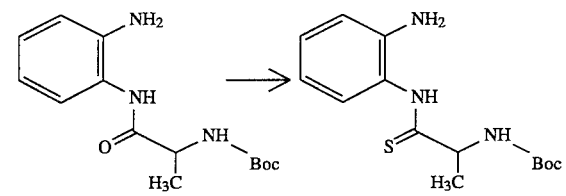

Under a flow of argon, phosphorus pentasulfide (0.75 g; 1.68 mmol) was mixed with sodium carbonate (0.18 g; 1.7 mmol) in dry THF (100 ml). The mixture was stirred for 1 hour at 25° C. and then cooled to 0° C. Boc-Alanyl-2-Aminoanilide (0.5 g; 1.79 mmol) (from example 1a) was added to this clear solution and the reaction was kept at this temperature overnight. To workup, an aqueous solution of sodium tribasic phosphate was added (12%, 7 ml) followed by EtOAc (20 ml) and heptane (20 ml). The organic layer was separated and washed with brine (2×30 ml). Solvent was then evaporated and the residue was purified on silica gel using EtOAc: hexanes (1:2) as eluant. This gave pure Boc-Alanyl-2-Aminothioanilide (0.28 g; 53%) as a pale yellow solid m.p. 124°–26° C., $R_f$=0.75 (EtOAc/hexanes 2:3), $^1$H NMR ($CDCl_3$) δ1.44 (s, 9H, 3×$CH_3$ Boc), 1.59 (d, 3H, $CH_3$, J=6.9 Hz), 3.94 (bs, 2H, $NH_2$), 4.62 (m, 1H, $H^α$), 5.35 (d, 1H, NH, J=6.87 Hz), 6.8 (m, 2H, aromatic), 7.15 (m, 2H, aromatic), 9.60 (bs, 1H, NH).

b) N-(Boc-Thioalanyl)-2-Benzimidazolone

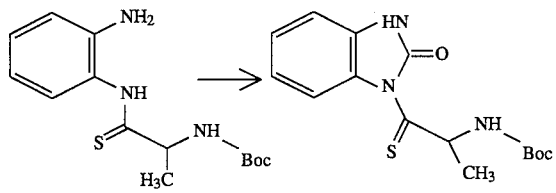

N-(Boc-Thioalanyl)-2-Benzimidazolone was prepared according to the procedure described in example 1b for N-(Boc-Alanyl)-2-Benzimidazolone, (0.30 g of Boc-Alanyl-2-Aminothioanilide (from example 2a), 0.99 mmol): yield (0.16 g; 51%); m.p. 101°–03° C., $R_f$=0.65 (EtOAc/ Hexanes 2:3), $^1$H NMR ($CDCl_3$) δ1.46 (s, 9H, 3×$CH_3$ Boc), 1.49 (d, 3H, $CH_3$, J=6.8 Hz), 5.55 (d, 1H, NH, J=6.87 Hz), 6.29 (m, 1H, $H^α$), 6.73–7.08 (m, 3H, aromatic), 8.65 (d, 1H, aromatic), 9.35 (bs, 1H, NH).

EXAMPLE 3

Preparation of Leuψ[CSNH]Phe-OH

Boc-Phe copolymer Merrifield Resin (0.632 m eq/g, 0.422 g, 0.28 mmol, BioChem Pharma) was treated with 55% TFA (10 ml) in $CH_2Cl_2$ (30 ml) for one hour at 25° C. Solvent was then removed and the resin was washed successively with $CH_2Cl_2$ (4×10 ml), isopropanol (4×10 ml) and 10% $Et_3N$ (1 ml) in MeOH under $N_2$. The presence of the free amino group was confirmed by Kaiser test. To the resin was added a solution of D- or L-Boc-Leu thioacylating reagents (1; R=$CH_2CH(CH_3)_2$, $R^1$=Boc) (0.15 g; 0.413 mmol, 1.5 eq.) in dry DMF (7 ml). After sixteen hours of stirring at 25° C., another portion of the thioacylating reagents (0.15 g, 0.143 mmol, 1.5 eq.) in dry DMF (7 ml) was added. The suspension was then stirred for eighty hours at 25° C. The peptide was cleaved from the resin and deprotected with HF at 0° C. The supernatant was filtered off and the resin was washed with methanol (2×10 ml). The organic layer was evaporated under reduced pressure and purified by HPLC using the system described above to afford the dipeptide (L)-Leu ψ[CSNH]Phe-OH (0.054 g, 95%) or (D)-Leu ψ[CSNH]Phe-OH (0.035 g, 90%) as a white solid material.

EXAMPLE 4

Preparation of Boc-Alanyl-2-N,N-dibenzylaminothioanilide a) Boc-Alanyl-2-N,N-dibenzylaminoanilide

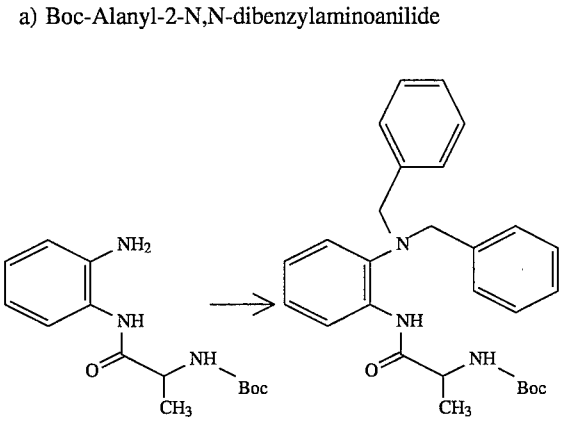

Triethylamine (0.07 ml; 0.5 mMol), followed by benzyl bromide (158 mg) were added to a solution of N-(Boc-Alanyl)-2-aminoanilide (example 1(a)) in dry THF (25 ml) kept at 0° C. under an atmosphere of argon. The solution was stirred at 25 ° C. overnight. The solvent was removed under reduced pressure and the crude product was purified on silica gel using ethyl acetate: hexanes (1:4) as eluant. Pure Boc-Alanyl-2-N,N-dibenzylaminoanilide (87 mg; 0.25 mMol; 54% yield) was recovered.

Rf: 0.4 (ethyl acetate: hexanes; 1:4) $^1$HNMR: (δCDCL$_3$ in ppm): 1.37 (d, 3H, $CH_3$), 1.48 (s, 9H, 3×$CH_3$, Boc), 4.06 (s, 4H, 2×$CH_2$), 4.25 (m, 1H, H$^α$), 5.02 (m, 1H, NH), 7.01–7.38 (m, 13H, aromatic), 8.23 (d, 1H, aromatic), 9.00 (bs, 1H, NH).

Mass spectrum: (FAB, thioglycerol, m/e) $M^+$=354 b) Boc-Alanyl-2-N,N-dibenzylaminothioanilide

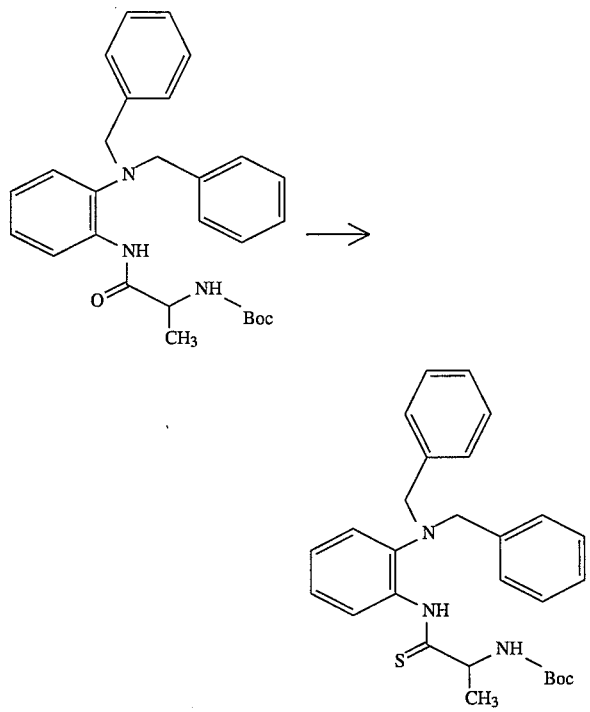

Boc-Alanyl-2-N,N-dibenzylaminoanilide (100 mg; 0.283 mMol) (example 4a) was dissolved in dry THF (20 ml). Lawesson's reagent (229 mg; 0.567 Mmol) was added to the solution and the reaction mixture was refluxed for 5 hours. The solvent was removed under reduced pressure and the residue was purified by chromatography on silica gel using 20% ethyl acetate/hexanes as eluant. Pure Boc-Alanyl-2-N,N-dibenzylaminothioanilide(54 mg; 0.15 mMol; 52% yield) was recovered.

Rf: 0.65 (20% ethyl acetate/hexanes)

$^1$HNMR: (δCDCL$_3$ in ppm) :1.37 (d, 3H, $CH_3$), 1.47 (s, 9H, 3×$CH_3$, Boc), 4.12 (s, 4H, 2×$CH_2$), 4.60 (m, 1H, H$^α$), 5.20 (m, 1H, NH), 7.00–7.41 (m, 13H, aromatic), 8.24 (d, 1H, aromatic), 9.25 (bs, 1H, NH).

EXAMPLE 5

Preparation of α-N-Boc-L-alanyl-L-valyl-L-alanyl-L-tyrosinyl-O-benzyl-benzyl ester-3-thioamide I. Synthesis of 1-(α-N-Boc-L-alanyl-L-valyl-thioacyl)-2-benzimidazolone a) Preparation of α-N-Boc-L-alanyl-L-valyl-ortho amino anilide α-N-Boc-L-alanyl-L-valyl benzyl ester (about 8 mmol) and ortho-phenylene diamine (about 11 mmol) are well dissolved in dichloromethane (20 ml) at 0° C. and N,N'-dicyclohexylcarbodiimide (DCC) (8 mmol) is added. The mixture is stirred for 1 hour at constant ice temperature and then filtered. The filtrate is transferred to a separating funnel and washed successively with saturated brine, 5% aqueous citric acid and 5% aqueous sodium bicarbonate, followed by saturated brine alone. The organic phase is then dried, concentrated, and the residue purified by flash chromatography on silica gel employing a 3:1 hexane-ethyl acetate solvent as an eluant to yield the α-N-Boc-L-alanyl-L-valyl-ortho amino anilide as a solid. The product is recrystallized to analytical purity with a dichloromethane/pentane mixture or alternatively, purified by flash chromatography on a silica gel column, using 1:1 hexane/ethyl acetate as the elutant.

b) Synthesis of α-N-Boc-L-alanyl-L-valyl-ortho amino thioanilide

Phosphorous pentasulfide (6.25 mmol) is added to freshly distilled tetrahydrofuran (THF) (70 ml) followed by anhydrous sodium carbonate (6.25 mmol). The mixture is stirred at 20° C. for 0.3 hours. The mixture is then cooled to 0° C., followed by the addition of the N-Boc-L-alanyl-L-valyl-ortho-amino anilide of step (a) (0.7 mmol). After standing at 0° C. for 5–6 hours, 10% aqueous sodium phosphate (tribasic; 20 ml) is added slowly followed by ethyl acetate (20 ml) and hexane (10 ml). The organic phase is separated, washed with brine, dried, and concentrated. The product oil may be purified by flash chromatography on silica gel using a 3:2 hexane/ethyl acetate eluant to give the α-N-Boc-L-alanyl-L-valyl-ortho amino thioanilide as a crystalline solid.

c) Synthesis of 1-(α-N-Boc-L-alanyl-L-valyl-thioacyl)-2-benzimidazalone

The α-N-Boc-L-alanyl-L-valyl-ortho amino thioanilide of step (b) (3 mmol) and carbonyl ditriazole (4 mmol) are dissolved in THF (45 ml) and after stirred at 25° C. for 6.5 hours. The solvent is then removed in vacuo. The remaining residue is dissolved in dichloromethane (2 ml) and purified by flash chromatography, eluting with 1:1 hexane/ethyl acetate to give pure 1-(α-N-Boc-L-alanyl-L-valyl-2-thioacyl)-2-benzimidazolone.

II. Coupling α-N-Boc-L-alanyl-L-tyrosinyl-O-benzyl ether benzyl ester with 1-(α-N-Boc-L-alanyl-L-valyl-thioacyl)-2-benzimidazolone a) Solution phase α-N-Boc-L-alanyl-L-tyrosinyl-O-benzyl ether benzyl ester is treated with trifluoroacetic acid (TFA) at 0° C. under a flow of nitrogen for 0.5 hours. The TFA is removed in vacuo to yield the L-alanyl-L-tyrosinyl-O-benzyl ether benzyl ester TFA salt. The TFA salt is then dissolved in methylene chloride and treated with 5% aqueous sodium bicarbonate. The organic phase is separated, dried and concentrated to give the free dipeptide derivative.

The resulting free peptide derivative (2 mmol) is dissolved in anhydrous N,N'-dimethylformamide (DMF, 0.5 ml) at 0° C. under nitrogen and 1-(α-N-Boc-L-alanyl-L-valyl-2-thioacyl)-2benzimidazolone (2.2 mmol) is added in portions at 0° C. with stirring over a 0.3 hour period. The mixture is stirred continuously at 0° C. for 2 hours and allowed to warm to 25° C. overnight. The reaction is then filtered and concentrated in vacuo. The residue is dissolved in ethyl acetate (15 ml) and the solution washed successively with 5% aqueous sodium bicarbonate, water, 5% aqueous citric acid and brine. The organic phase is then dried, followed by evaporation and the residue is placed on a flash column of silica gel for purification using 1:1 hexane/ethyl acetate as the elutant.

b) Solid phase

α-N-Boc-L-alanyl-L-tyrosinyl-O-benzyl ether attached to a benzyloxy group of a Merrifield resin is treated with 55% dichloromethane solution of TFA at room temperature for 1 hour. The resin is then collected, washed successively with four portions of 10 ml dichloromethane, four portions of 10 ml isopropanol (IPA) and dried for subsequent use.

L-alanyl-L-tyrosinyl-O-benzyl ether attached to a benzyloxy group of a Merrifield resin (0.6 mmol/g of resin) is added to a solution of 1-(α-N-Boc-L-alanyl-L-valyl-2-thioacyl)-2-benzimidazolone (1 mmol) in dry DMF (7 ml) with stirring at 25° C. The reaction is stirred for 16 hours after which time another portion of the benzimidazolone (1 mmol) is added and stirring resumed for 18 hours. The α-N-Boc-L-alanyl-L-valyl-L-alanyl-L-tyrosinyl-O-benzyl ether-3-thioamide-resin ester is collected, washed with four 10 ml portions of DMF, then four 10 ml portions of IPA and subsequently dried in preparation for further reaction.

α-N-Boc-L-alanyl-L-valyl-L-alanyl-L-tyrosinyl-O-benzyl ether-3-thioamide-resin ester (0.5 mmol) is treated with liquid hydrogen fluoride (5 ml) containing anisole, dimethyl sulfide, and thioanisole (0.5 ml 1:1:1 v/v) at 0° C. for 1 hour. After evaporation of the solvent, the residue is dissolved in 10% aqueous acetic acid. The aqueous solution is washed with diethyl ether (30 ml), eluted with water and lyophilized to dryness. The crude product is dissolved in 92% aqueous acetic acid (25 ml) and purified by reverse phase chromatography employing a $C_{18}$ packed column and the same acetic acid solvent as the eluant to give α-N-Boc-L-alanyl-L-valyl-L-alanyl-L-tyrosinyl-O-benzyl ether-3thioamide.

EXAMPLE 6

Preparation of a Terminus-to-Terminus Cyclic Thiopeptide: Cyclic 1-thio-L-alanyl-L-alanine 1-(α-N-Boc-L-alanyl-L-alanyl-thioacyl)-2-benzimidazolone, prepared according to the procedure described in Example 1, is treated with trifluoroacetic acid (TFA) at 0° C. under nitrogen for 1 hour. The TFA is removed in vacuo to yield the TFA salt of the dipeptide. The TFA salt is dissolved in dichloromethane and treated with 5% aqueous sodium bicarbonate. The organic phase is separated, dried and concentrated. DMF is added and the reaction is stirred overnight. The solution is then evaporated under reduced pressure and the residue is purified by silica gel flash chromatography, using 1:1 hexane/ethyl acetate as the elutant, to yield the terminus-to-terminus cyclic thiopeptide, cyclic 1-thio-L-alanyl-L-alanine.

EXAMPLE 7

Preparation of a Side Chain Cyclized Thiopeptide: Cyclic β-cysteinyl-S-2-thioalanine 1-(α-N-Boc-L-cysteinyl-S-tert-butyl-L-alanyl-thioacyl)-2-benzimidazolone, prepared according to the procedure described in Example 1, is treated with TFA at 0° C. under argon for 2 hours. The TFA is evaporated under high vacuum to yield the corresponding TFA salt. The TFA salt is dissolved in dichloromethane and treated with 5% aqueous sodium bicarbonate. The organic phase is separated, dried and concentrated. DMF is added and the reaction is stirred for 18 hours. The solution is then evaporated under reduced pressure and the solid is purified by flash chromatography, using 1:1 hexane/ethyl acetate as the elutant, to yield the desired side chain cyclized thiopeptide, cyclic β-cysteinyl-S-2-thioalanine.

EXAMPLE 8

Preparation of α-N-Boc-L-alanyl-L-alanyl methyl ester-1-thioamide

Thiocarbonyldiimidazole (80mg, 0.45 mmol) was added in one portion to a solution of α-N-Boc-L-alanyl-2-aminothioanilide (105 mg, 0.37 mmol) in dry THF (20 ml) under an argon flow. The resulting pale yellow solution was stirred at 25 ° C. for 10 min. L-alanyl methyl ester (51 mg; 0.49 mMol) was then added and the mixture was stirred at room temperature overnight. The solvent was evaporated under reduced pressure and the residue was triturated with ethyl acetate (2×20 ml). The suspension was filtered and the solvent evaporated under high vaccum. The resulting residue was purified by chromatography on silica gel using ethyl acetate: hexanes (1:1) as an eluant to yield to pure α-N-Boc-L-alanyl-Lalanyl methyl ester-1 thioamide (50 mg, 0.172 mmol, 47% yield) as a white solid.

Rf (0.4, Ethyl acetate:hexanes :2:3) HRMS (275) $C_{10}H_{21}N_5O_4$ calculated:275.15990 found: 275.15936

I claim:

1. A method for producing a linear thiopeptide comprising step (3):

contacting a peptide or an amino acid residue with a mixture comprising an amino acid ortho amino thioanilide of formula (III):

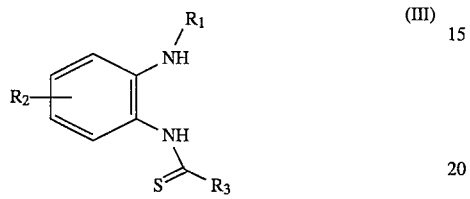

and an amino reactive compound suitable for internal ring closure in an inert organic solvent (a);

wherein $R_1$ is selected from the group consisting of hydrogen, $C_1$-$C_4$ branched or unbranched alkyl, and an appropriate amino protecting group;

$R_2$ is selected from the group consisting of hydrogen, halo, amino, hydroxy, $C_1$-$C_4$ branched or unbranched alkoxy, guanido, amido, acyl, carboxy, cyano, mercapto, nitro, azido, and $C_1$-$C_4$ branched or unbranched alkyl, unsubstituted or substituted with halo, amino, hydroxy, $C_1$-$C_4$ branched or unbranched alkoxy, guanido, amido, acyl, carboxy, cyano, mercapto, nitro, azido; and $R_3$ is a decarboxylated amino acid residue or a decarboxylated amino acid chain having at least two amino acid residues.

2. The method according to claim 1 wherein $R_1$ and $R_2$ are hydrogen.

3. The method according to claim 1 wherein $R_3$ has between 1 and 15 amino acid residues.

4. The method according to any one of claims 1 to 3 wherein said inert organic solvent (a) is selected from the group consisting of dichloromethane, diethyl ether, chloroform, N,N'-dimethylformamide and tetrahydrofuran.

5. The method according to claim 1 or 4 wherein said amino reactive compound is selected from the group consisting of carbonyldiimidazole, thiocarbonyldiimidazole, carbonylditriazole, thiocarbonylditriazole and phosgene.

6. The method according to claim 4 wherein said amino reactive compound is thiocarbonyldiimidazole.

7. The method according to claim 5 wherein step (3) is carried out at a temperature of –78° C. to reflux for a period of 1 to 48 hours.

8. The method according to claim 5 wherein step (3) is carried out at a temperature of –10° C. to 25° C. for a period of 4 to 6 hours.

9. The method according to claim 6 wherein step (3) is carried out at a temperature of –78° C. to reflux for a period of 1 to 48 hours.

10. The method according to claim 6 wherein step (3) is carried out at a temperature of –10° C. to 25° C. for a period of 4 to 6 hours.

11. The method according to claim 1 wherein said amino acid ortho amino thioanilide of formula (III)

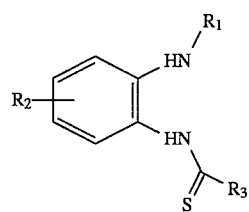

wherein $R_1$, $R_2$, and $R_3$ are as defined in claim 1; is produced by step (2):

contacting an amino acid ortho amino anilide of formula (II):

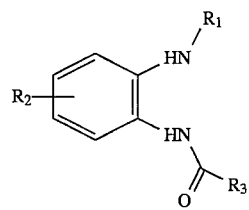

wherein $R_1$, $R_2$, and $R_3$ are as defined above, with a thionation reagent in an inert organic solvent (b).

12. The method according to claim 11 wherein $R_1$ and $R_2$ are hydrogen.

13. The method according to claim 11 wherein $R_3$ has between 1 and 15 amino acid residues.

14. The method according to claim 11 wherein said thionation reagent is Lawesson's reagent or a mixture of phosphorous pentasulfide and sodium carbonate.

15. The method according to any one of claims 11 to 14, wherein the inert organic solvent (b) is selected from the group consisting of diethyl ether and tetrahydrofuran.

16. The method according to claim 15 wherein step (2) is carried out at a temperature of –78° C. to reflux for a period of 1 to 48 hours.

17. The method according to claim 15 wherein step (2) is carried out at a temperature of –10° C. to 25° C. for a period of 4 to 6 hours.

18. The method according to claim 11 wherein the amino acid ortho amino anilide of formula (II) is produced by step (1):

contacting $R_3COOH$ with an ortho phenylene diamine of formula (I):

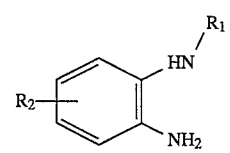

in the presence of a peptide coupling agent in an inert organic solvent (c), wherein $R_1$, $R_2$ and $R_3$ are defined according to claim 11.

19. The method according to claim 18 wherein $R_1$ and $R_2$ are hydrogen.

20. The method according to claim 18 wherein $R_3$ has between 1 and 15 amino acid residues.

21. The method according to any one of claims 18 to 20 wherein the inert organic solvent (c) is selected from the group consisting of dichloromethane, chloroform, N,N'- dimethylformamide and tetrahydrofuran.

22. The method according to claim 21 wherein the peptide coupling agent is selected from the group consisting of N,N'-dicyclohexylcarbodiimide, N,N'-carbonyl diimidizole, 1-hydroxybenzotriazole, ethyl chloroformate, benzyl chloroformate and 1-3(3-dimethylaminopropyl)-3-ethylcarbodiimide (EDC).

23. The method according to claim 22 wherein step (1) is carried out at a temperature of −78° C. to reflux for a period of 1 to 48 hours.

24. The method according to claim 22 wherein step (1) is carried out at a temperature of −10° C. to 25° C. for a period of 4 to 6 hours.

* * * * *